US012256757B2

(12) United States Patent
Cocchi et al.

(10) Patent No.: US 12,256,757 B2
(45) Date of Patent: Mar. 25, 2025

(54) METHOD AND APPARATUS FOR CONTROLLING THE QUALITY OF FOOD PRODUCTS AND SYSTEM FOR TREATING FOOD PRODUCTS COMPRISING THE APPARATUS

(71) Applicant: ALI GROUP S.R.L.—CARPIGIANI, Cernusco sul Naviglio (IT)

(72) Inventors: Andrea Cocchi, Bologna (IT); Federico Tassi, Bologna (IT); Roberto Lazzarini, Reggio Emilia (IT)

(73) Assignee: ALI GROUP S.R.L.—CARPIGIANI, Cernusco sul Naviglio (IT)

( * ) Notice: Subject to any disclaimer, the term of this patent is extended or adjusted under 35 U.S.C. 154(b) by 0 days.

(21) Appl. No.: 17/713,450

(22) Filed: Apr. 5, 2022

(65) Prior Publication Data
US 2022/0322695 A1    Oct. 13, 2022

(30) Foreign Application Priority Data

Apr. 7, 2021   (IT) .................. 102021000008717

(51) Int. Cl.
*A23G 9/22*    (2006.01)
*A23L 3/00*    (2006.01)
(52) U.S. Cl.
CPC .............. *A23G 9/228* (2013.01); *A23L 3/003* (2013.01); *A23V 2002/00* (2013.01)
(58) Field of Classification Search
CPC ................................ A23G 9/228; A23L 3/003
See application file for complete search history.

(56) References Cited

U.S. PATENT DOCUMENTS

| 10,022,614 B1* | 7/2018 | Tran ................. G16H 50/20 |
| 10,801,734 B2* | 10/2020 | Bhogal ................. A23L 5/17 |
| 2005/0193901 A1* | 9/2005 | Buehler ................. A23L 5/10 99/468 |
| 2012/0312049 A1 | 12/2012 | Downs et al. |

(Continued)

FOREIGN PATENT DOCUMENTS

| CN | 108168178 A | 6/2018 |
| EP | 2783574 A1 | 10/2014 |

(Continued)

OTHER PUBLICATIONS

Italian Search Report dated Nov. 29, 2021 from counterpart Italian Patent Application No. 102021000008717.

*Primary Examiner* — Steven N Leff
(74) *Attorney, Agent, or Firm* — SHUTTLEWORTH & INGERSOLL, PLC; Timothy J. Klima

(57) ABSTRACT

Described is an apparatus for controlling the quality of a food product, including a quality control module, equipped with:
at least one sensorized device, the sensorized device being adapted to detect at least one parameter regarding a property of a food product;
a processing and control unit connected to the sensorized device for receiving the detected value regarding a property of a food product; the processing unit is configured to derive a quality indication of the food product based on the value detected by the sensorized device, and the apparatus includes a communication module connected to the processing and control unit and configured to transmit information relating to the derived quality indication.

22 Claims, 3 Drawing Sheets

(56) References Cited

U.S. PATENT DOCUMENTS

| | | | | |
|---|---|---|---|---|
| 2016/0316524 A1* | 10/2016 | Franchi | ............... | H05B 6/6473 |
| 2018/0324908 A1* | 11/2018 | Denker | ................. | H04N 7/188 |
| 2019/0110638 A1* | 4/2019 | Li | ............................ | A23L 5/15 |
| 2019/0121350 A1 | 4/2019 | Cella et al. | | |
| 2020/0018551 A1* | 1/2020 | Hur | ........................ | F27D 21/02 |
| 2020/0363778 A1 | 11/2020 | Mahapatra | | |
| 2021/0022547 A1 | 1/2021 | Stork genannt Wersborg | | |

FOREIGN PATENT DOCUMENTS

| | | |
|---|---|---|
| EP | 3521705 A1 | 8/2019 |
| EP | 3789850 A1 | 3/2021 |
| WO | 2020060380 A1 | 3/2020 |

\* cited by examiner

METHOD AND APPARATUS FOR CONTROLLING THE QUALITY OF FOOD PRODUCTS AND SYSTEM FOR TREATING FOOD PRODUCTS COMPRISING THE APPARATUS

This application claims priority to Italian Patent Application 102021000008717 filed Apr. 7, 2021, the entirety of which is incorporated by reference herein.

The invention relates to a method and an apparatus for controlling the quality of food products (of any kind) and to a system for treating food products comprising the apparatus.

In the sector concerned, there is a particularly strongly felt need for users who serve food products to be able to automatically check the quality of the food products in order to control product quality, ensure repeatability and increase product quality standards for the users themselves and/or for their end customers.

In the food sector, there is, in particular, a strongly felt need for a repeatable measurement of quality which can give the same results for identical products.

The purpose is to provide users and/or end customers with products of better and better quality and that is safe and controlled in terms of food safety.

This invention therefore has for an aim to meet the above need by providing an apparatus for controlling the quality of food products and a system for treating food products comprising the apparatus.

Another aim of this invention is to provide a method for controlling the quality of food products.

The technical features of the disclosure, with reference to the above aims, are clearly described in the claims below and its advantages are apparent from the detailed description which follows, with reference to the accompanying drawings which illustrate a preferred, non-limiting example embodiment, and in which:

FIG. 1 shows a schematic view of a quality control apparatus according to this invention;

FIG. 2 schematically illustrates a food product processing system that incorporates the quality control apparatus of FIG. 1;

Figure 1:
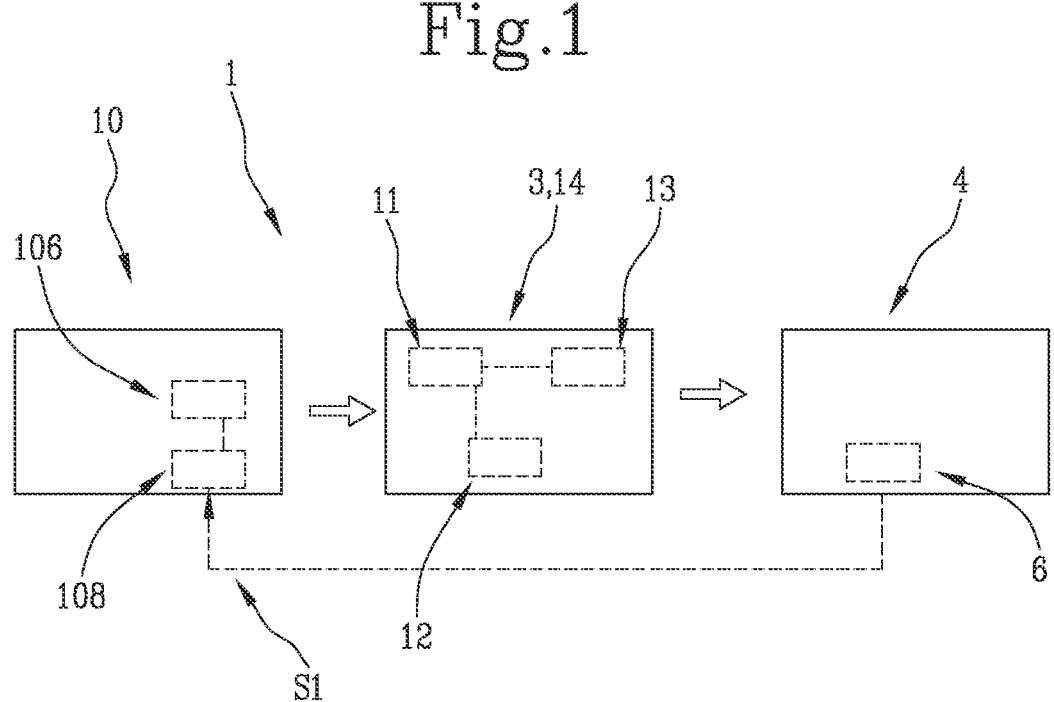
Figure 2:
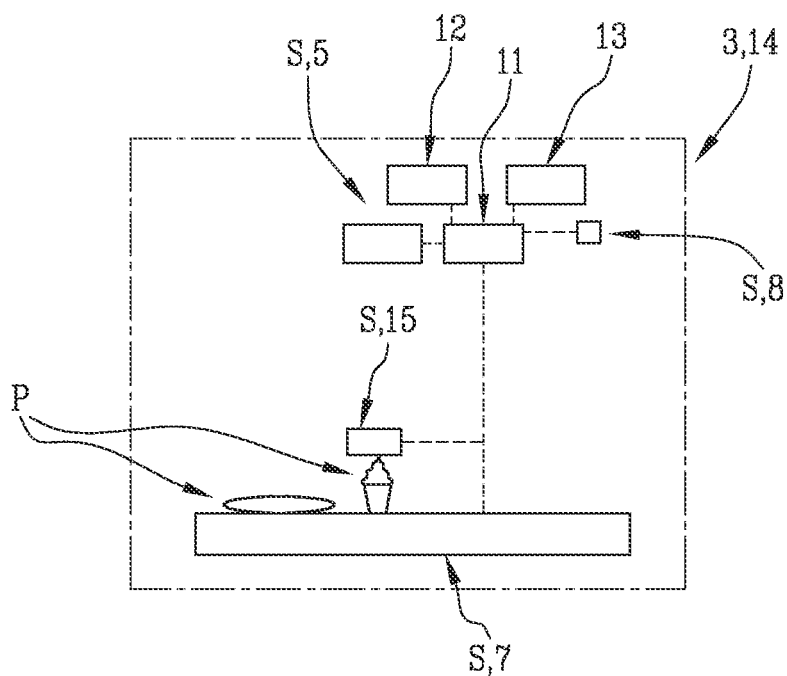

Defined according to the invention is an apparatus 3 for controlling the quality of a food product, comprising a quality control module 14, equipped with:
  at least one sensor S, the sensor S being adapted to detect at least one parameter regarding a property of a food product P;
  a processor 11 connected to the sensor S for receiving the detected value regarding a property of a food product.

According to an aspect, the processor 11 is configured to derive a quality indication (in qualitative or quantitative form) relating to the food product P and based on the value detected by the sensor S.

The expression "quality indication" is used to mean any piece of information relating to the quality of the food product, meaning a piece of information regarding both quality, expressed in the form of an assessment, and quantity (derived from the parameter detected by the sensor S).

According to another aspect, the quality control module 14 comprises a communication module 12 connected to the processor 11 and configured to transmit information relating to the derived quality indication.

According to an aspect, the processor 11 comprises an artificial intelligence algorithm configured to derive a quality indication of the food product P based on the value detected by the sensor S.

The expression "artificial intelligence" is used to mean any computer algorithm configured to modify its (computer) operating configuration based on a set of experimental data presented to it.

The algorithm might, by way of non-exhaustive example, be a neural network.

More generally speaking, the artificial intelligence algorithm might be a strong or weak artificial intelligence algorithm.

According to another aspect, the sensor S comprises one or more of the following elements: a weight sensor 7 for detecting the weight of the food product; a temperature sensor 8 for detecting the temperature of the food product.

According to yet another aspect, the sensor S comprises at least one weight sensor 7.

According to yet another aspect, the sensor S comprises a temperature sensor 8 (preferably a thermoscanner).

According to yet another aspect, the sensor S comprises a hygrometer, adapted to measure the humidity of the air.

According to yet another aspect, the sensor S comprises one or more biosensors 15, adapted to measure the chemical composition of the food product P.

According to another aspect, the apparatus 3 comprises a colorimeter to assess the surface state of the food product P.

According to yet another aspect, the sensor S comprises a video capturing system 5, configured to capture at least one image of the food product.

According to this aspect, the processor 11 is configured to recognize the type of food product based on the at least one image captured.

According to another aspect, the processor 11 is configured to assess the shape and/or the colours and/or the surface aspect of the food product P (preferably based on the image captured).

It should be noted that the processor 11 is configured, preferably, to compare the value of the parameter detected by one or more sensors with stored parameter values (and, if the apparatus 3 can work with two or more products and is configured to recognize the product, preferably relating to the recognized type).

According to yet another aspect, the artificial intelligence algorithm is a machine learning algorithm and the processor 11 is configured to perform a self-learning process in which each food product P for which the sensor S has detected the at least one parameter relating to a property of a food product P (for example, a physicochemical and/or organoleptic property such as colour, form, temperature, relative humidity, impedance, overrun, etc.), is associated with a quality parameter value (for example, relating to its acceptability or unacceptability) entered by a user and/or the assessing system through an interface.

This quality parameter value—entered by the user and/or by the assessing system through a user interface (or automatically) forming part of the apparatus 3—is transmitted to the processor 11.

In practice, an operator uses the user interface of the apparatus 3 to assign a quality parameter value to each food product P.

The artificial intelligence algorithm is a machine learning algorithm and uses the quality parameter value in association with the detected values of a parameter relating to a property of a food product P to adapt its model (that is to say, to modify its configuration according to a learning process).

In short, in this learning process, samples of food products are presented to the sensor S which measures at least one parameter relating to a property of the food product P and each sample is associated with a quality parameter value (relating to its quality and/or its acceptability or unacceptability).

According to yet another aspect, the artificial intelligence algorithm is a machine learning algorithm and comprises a neural network.

According to yet another aspect, the apparatus 1 comprises a feedback device 4 provided with a user interface 6 configured to allow sending to the processor 11 a parameter value relating to a quality assessment associated with the food product P.

The parameter value relating to a quality assessment associated with the food product P is, for all intents and purposes, feedback from the operator and/or the end customer.

According to this aspect, the processor 11 may comprise an algorithm configured to use data mining techniques to extract behavioural patterns from the quality assessment parameter values.

The feedback device 4 is preferably a personal digital assistant, a mobile phone, a tablet or a PC and is used by the consumer to enter an assessment of the food product P consumed.

Also defined according to the invention is a production system 1 for making a food product and comprising:
- a machine 10 adapted to thermally treat a food product, equipped with at least one actuator (104, 116) operating on the food product and a control unit 106 that controls the at least one actuator (104, 116);
- a control apparatus 3 as described in the foregoing.

The system 1 described is connectable to a traceability system which, for improved end product quality assurance, allows tracking both the raw materials and the processing equipment/machinery.

The values of the properties of interest for each of the raw materials and pieces of equipment are precisely detected-specifically by sensors-so as to be able to start processing.

It should be noted that the processor 11 of the apparatus is connected to the control unit 106 of the machine 10 to send control and adjustment signals S1 to it based on the derived quality indication of the food product and the control unit 106 of the machine 10 is configured to adjust the at least one actuator (104, 116) based on the control and adjustment signals S1.

That way, a feedback loop is established between the control apparatus 3 and the machine 10 to adapt the processing parameters based on the result of the check carried out by the control apparatus 3.

According to another aspect, the processor 11 of the apparatus 3 is configured to send control and adjustment signals S1 based on the derived parameter relating to the quality assessment.

The machine 10 is described below with reference in particular to FIG. 3.

The machine 10 may be any machine for making or processing food products.

Hereinafter, however, with reference in particular to FIG. 3 the machine 10 will be described, for simplicity and ease of understanding and without losing in generality, as a machine designed to treat liquid or semi-liquid products (thermally)—suitable, for example, to perform a thermal treatment such as pasteurization, or for making an ice cream product.

Figure 3:
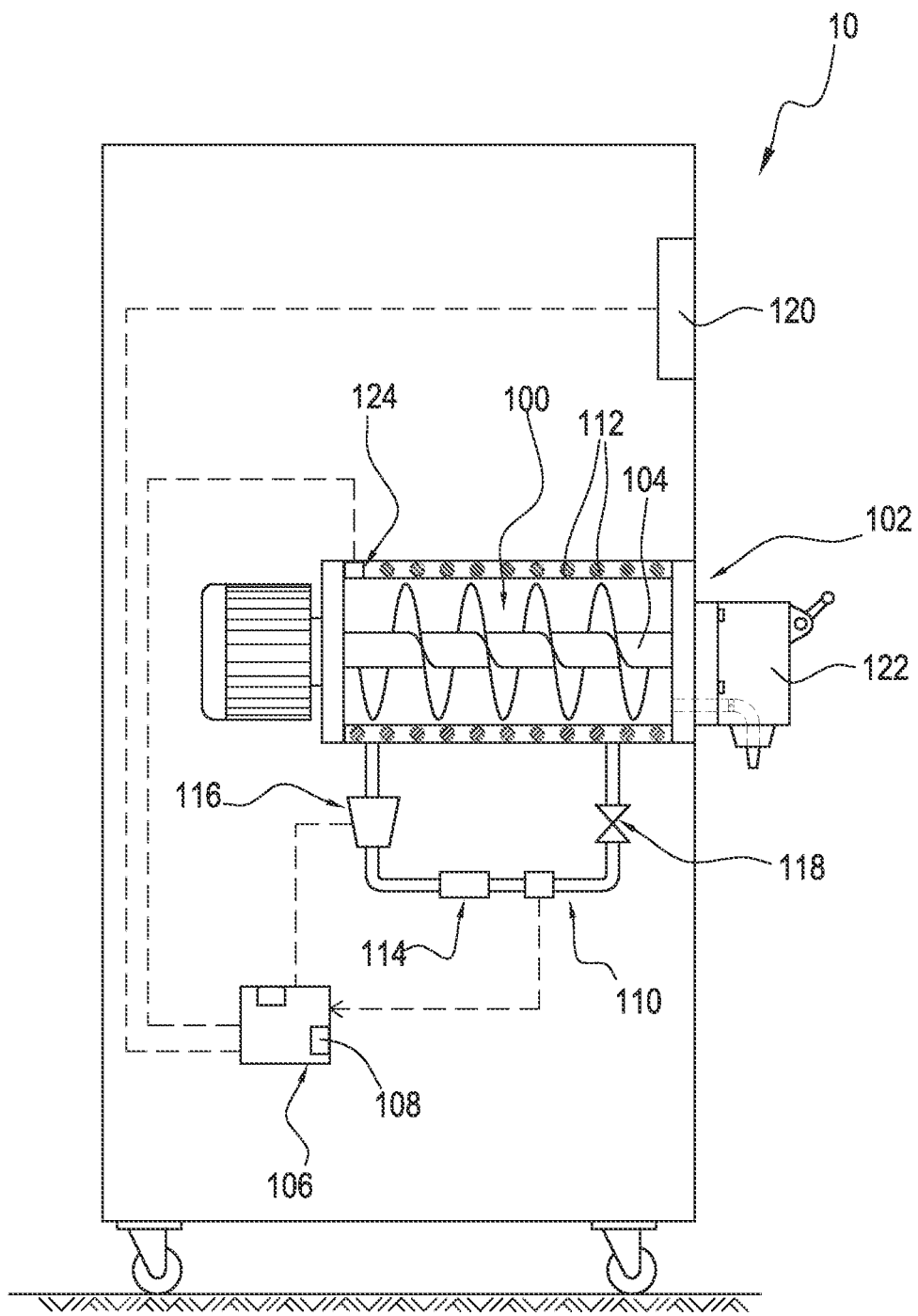
FIG. 3 shows a machine to which the quality control apparatus of FIG. 1 can be applied.
Figure 4:
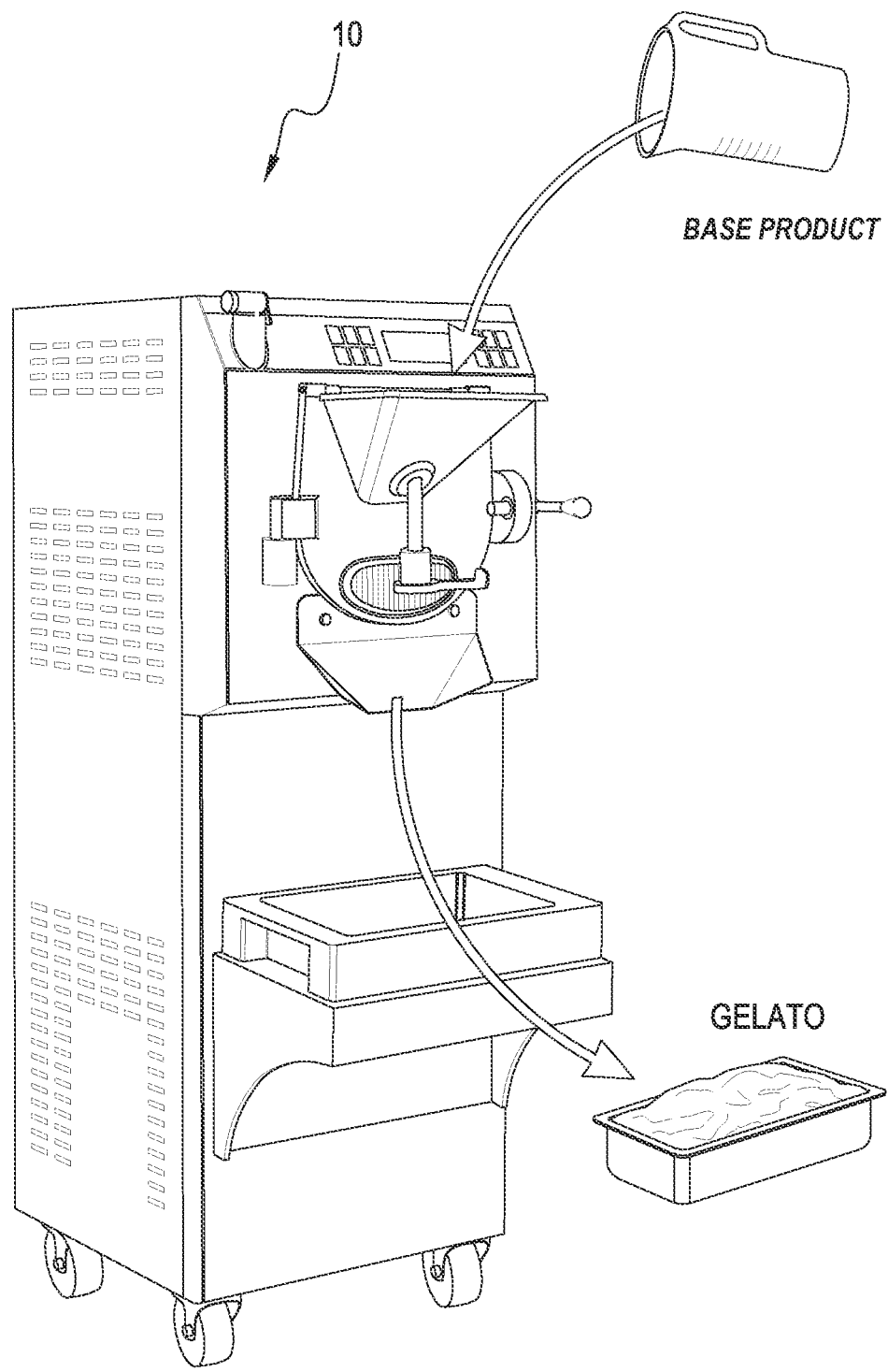
FIG. 4 shows a machine to which the quality control apparatus of FIG. 1 can be applied.

The machine 10 for treating liquid or semi-liquid food products illustrated in FIG. 3 is preferably a machine for making products of the sector of ice cream, bakery and confectionery and the like (by way of non-limiting example: gelato, soft serve ice cream, granitas, sorbet, milk shakes, yogurt, frozen desserts, chilled creams) and may thus comprise a machine for making ice cream (soft serve or artisan gelato) provided with a container for thermal treatment (pasteurization).

The machine 10 for treating food products such as, for example, liquid or semi-liquid products, comprises a treatment chamber 100, configured to receive a food product.

As illustrated in FIG. 3, the machine 10 may preferably comprise a container 102 for processing a liquid or semi-liquid base product and defining the treatment chamber 100.

The machine 10 further comprises at least one actuator 104 configured to apply a treatment process to the food product inside the treatment chamber 100.

As illustrated in FIG. 3, the actuator 104 may preferably comprise a stirrer (preferably mounted inside the container 102) to mix the product inside the treatment chamber 100.

The machine 10 of FIG. 3 also comprises a controller 106 and a data exchange module 108.

By "actuator", as used in this disclosure, is meant any mechanical, electrical, electronic or other element operating on the food product to perform a process on it (of any kind: mechanical, thermal, or chemical, for example).

According to an aspect, the actuator 104 may be defined by one or more heating and/or cooling elements.

The machine 10 for treating food products, as illustrated in FIG. 3, may also comprise a thermal treatment system 110, comprising a heat exchanger 112 associated with the processing container 102.

As illustrated in the non-limiting example of FIG. 3, the machine 1 may comprise a motor connected to the stirrer 104 to drive the stirrer in rotation.

Preferably, the motor is connected to the controller 106.

According to another aspect, the thermal system 110 comprises a heat exchanger 112 associated with the processing container 102, a further heat exchanger 114, a compressor 116 and a pressure reducing element 118. It should be noticed that the heat exchanger 112, the further heat exchanger 114, the compressor 116, and the pressure reducing element 118 define a circuit containing a heat exchanger fluid.

In other words, the thermal system 110 is a thermodynamic system (configured to operate according to a thermodynamic cycle using a heat exchanger fluid).

According to another aspect, the machine 10 comprises a user interface 120 comprising at least one user-operable control (preferably a plurality of controls) and connected to the controller 106.

Preferably, the interface 120 comprises user-operable activation and selection controls and/or pushbuttons.

According to yet another aspect, the machine 10 comprises a dispenser 122, which is connected to the processing container 100 for processing a liquid or semi-liquid base product, and which allows the product to be extracted from the container 100. The dispenser 122 preferably comprises a user-operable lever to allow dispensing the treated product.

More generally speaking, the machine 10 may be a machine for treating food products of any kind: for example, it may be an oven, a refrigerator, a kneading machine, a machine for the ice cream/bakery and confectionery trade or other machine.

If the machine 10 for treating food products is an oven, the machine 10 may comprise one or more of the following elements:
- one or more heating elements configured to thermally treat the food product (and, in this disclosure, also referred to as "actuators" operating on the product),
- one or more elements for adjusting the product processing temperature,
- one or more elements to allow adjusting one or more thermal cycles on the product,
- one or more elements for adjusting the speed and on/off time cycle of fans,
- one or more elements for controlling and adjusting the humidity inside the oven.

According to an aspect of the invention, the controller 106 is configured to drive the actuator (or the actuators if the machine 10 comprises a plurality of actuators), for example by switching it on and off and/or by modifying its operating state.

According to another aspect, the apparatus 3 comprises a database 13, connected to the processor 11 and configured to store at least the derived quality indication and/or the detected value of the at least one parameter regarding a property of a food product P detected by the sensor S.

It should be noted that the database 3 may be a centralized or distributed (cloud) database.

Advantageously, the database 3 may be used to store information regarding the traceability of the production process of the food product P: in effect, it may contain all the information detected by the control apparatus 3, or derived therefrom, and/or the information entered by the users through the respective interfaces.

Defined according to the invention is a method (for controlling the quality of a food product or for treating a food) comprising the following steps:
- detecting with a sensor S at least one parameter regarding a property of a food product P;
- deriving a quality indication of the food product P based on the value detected by the sensor;
- transmitting the quality indication through a data communication network.

According to an aspect, deriving is performed by an artificial intelligence algorithm.

By "treating a food", as used in this disclosure, is meant any action—for example, thermal, mechanical, chemical, cleaning or of any other kind—carried out on the food product for the purposes of processing.

For example, the treatment may comprise an act of cooking a food product.

For example, the treatment may comprise an act of batch freezing a food product (stirring and cooling it simultaneously).

Also defined according to the invention is a method wherein the step of detecting with a sensor S at least one parameter regarding a property of a food product P comprises a step of capturing at least one image of the food product P by means of a video capturing system 5, and wherein the method further comprises the step of:
- processing the image captured by the video capturing system 5 (preferably but not necessarily by means of the artificial intelligence algorithm) and, based on that image, determining a type for the food product P.

According to another aspect, the step of detecting with a sensor S at least one parameter regarding a property of a food product P comprises a step of detecting a temperature of the food product P.

According to yet another aspect, the step of detecting with a sensor S at least one parameter regarding a property of a food product P comprises a step of detecting a weight of the food product P.

According to another aspect, the step of detecting with a sensor S at least one parameter regarding a property of a food product P comprises a step of detecting a form and/or a shape and/or the colours of the food product P.

According to another aspect, the step of detecting with a sensor S at least one parameter regarding a property of a food product P comprises a step of detecting a humidity and/or a temperature of the air.

According to another aspect, the step of detecting with a sensor S at least one parameter regarding a property of a food product P comprises a step of detecting a chemical composition of the food product P.

According to yet another aspect, the method comprises the following steps:
- preparing a machine 10 adapted to thermally treat the food product P, equipped with at least one actuator (104, 116) operating on the food product and a control unit 106 that controls the at least one actuator (104, 116);
- sending control signals S1 to the control unit 106 that controls the at least one actuator (104, 116) and adjusting the at least one actuator (104, 116) as a function of the derived quality indication.

According to another aspect, the actuator is a heating and/or cooling element and wherein the step of adjusting the at least one actuator (104, 116) as a function of the derived quality indication comprises a step of adjusting a thermal power of the heating and/or cooling element.

According to yet another aspect, the step of adjusting the at least one actuator (104, 116) as a function of the derived quality indication comprises a step of adjusting a processing time of the food product in the machine 10.

According to yet another aspect, the method comprises a step of measuring at least one parameter regarding base ingredients of the food product.

Preferably, the parameter regarding base ingredients of the food product comprises one or more of the following values: weight, colour, form, consistency, viscosity, transparency, volume, chemical composition, air humidity, air temperature.

According to an aspect, the parameter regarding base ingredients of the food product and the parameter detected with a sensor S relate to the same physical quantity (that is, they are both measurements of the same physical quantity, for example, weight, temperature, etc.) and the method comprises a step of comparing the measured values of the parameter regarding base ingredients of the food product and the parameter detected with a sensor S.

According to yet another aspect, the step of measuring at least one parameter regarding base ingredients of the food product comprises a step of measuring a weight of the base ingredients and the step of detecting at least one parameter regarding a property of a food product P comprises a step of measuring a weight of the food product P, the method further comprising a step of comparing the measured weight of the base ingredients with the measured weight of the food product P.

According to yet another aspect, the step of deriving a quality indication of the food product P based on the value detected by the sensor comprises a step of running an algorithm (preferably a machine learning algorithm) in a self-learning mode, wherein input for the algorithm in the self-learning mode is the value of a parameter representing a quality assessment associated with the food product and entered by a user (customer or operator) through a feedback device 4. More generally speaking, for each single food product P it is possible to combine the quality indication obtained by the sensor S with the quality assessment entered by the user through the interface of the feedback device 4 and to compare it with the average of the preceding food products P to obtain a final quality indication.

According to this aspect, the final quality indication (Ifin) of the n-th food product is calculated as follows:

$$Ifin=(G_{op}+I_n)/Imed_{n-1}$$

Where:

$Imed_{n-1}$ is the average final quality indication of the preceding food products P;

$G_{op}$ is the quality assessment of the end operator (customer and/or user);

$I_n$ is the quality indication obtained by the sensor S.

If the quality assessment of the end operator (customer and/or user) is not used in the method, then $G_{op}=0$.

According to an aspect, the final quality indication Ifin will preferably be compared with a predetermined threshold value (for example, <1 unacceptable, >1 acceptable).

According to this aspect, the processor 11 is configured to combine the quality indication obtained by the sensor S with the quality assessment entered by the user through the interface of the feedback device 4, to calculate a final quality indication.

Further, the processor 11 is configured to calculate, for a given food product P, a final quality indication based also on a mean final quality indication of the food products controlled previously.

According to another aspect, the method comprises combining the quality indication obtained by the sensor S with the quality assessment entered by the user through the interface of the feedback device 4, to calculate a final quality indication.

The method also comprises calculating a final quality indication, for a given food product P, based also on a mean final quality indication of the food products P controlled previously.

Advantageously, as disclosed herein, an apparatus and a method are provided to allow controlling the quality of a food product in an extremely simple and automated manner.

Furthermore, as disclosed herein, it is also possible to adjust the machine parameters which affect the property/properties measured by the apparatus or detected according to the method in order to increase the quality of the food product P through a feedback process.

The invention claimed is:

1. A production system for making a liquid or semi-liquid food product, comprising:
a machine for treating the food product, the machine adapted to thermally treat the food product, including at least one actuator operating on the food product;
a controller that controls the at least one actuator;
a container for processing the food product and defining a treatment chamber;
the at least one actuator including a stirrer and being configured to apply a treatment process to the food product inside the treatment chamber, the stirrer being mounted inside the container to mix the product inside the treatment chamber;
a quality control apparatus for controlling a quality of the food product, comprising;
a quality control module, comprising:
a sensor to detect at least one parameter regarding a property of the food product and/or a property of a processing environment, among a physico-chemical and/or organoleptic property, color, form, temperature, relative humidity, impedance, or overrun of the food product;
a processor connected to the sensor for receiving a detected value of the at least one parameter regarding the property of the food product;
the processor being configured to derive a quality indication of the food product based on the detected value, the quality indication including information relating to a quality of the food product, expressed as an assessment of the quality, relating to the at least one parameter,
a communication module connected to the processor and configured to transmit information relating to the derived quality indication;
the communication module being connected to the controller of the machine to send control and adjustment signals to the machine based on the derived quality indication of the food product and the controller of the machine being configured to adjust the at least one actuator based on at least one of the control and adjustment signals;
a feedback device connected between the processor and the controller of the machine, including a user interface configured to allow a user to send to the processor a parameter representing a quality assessment of the food product used during a self-learning mode; and
wherein the processor combines the derived quality indication of the food product based on the detected value, the quality assessment of the food product obtained from the user during a self-learning mode, and an average final quality indication of preceding foods product to obtain a final quality indication according to the following:

$$I_{fin}=(G_{op}+I_n)/I_{medn-1}$$

wherein, $I_{fin}$ is the final quality indication of the food product;

$I_{medn-1}$ is the average final quality indication of the preceding food products;

$G_{op}$ is the quality assessment from the user in the self-learning mode; and $I_n$ is the quality indication derived from the sensor.

2. The production system according to claim 1, wherein the sensor comprises at least one chosen from the following elements: a weight sensor for detecting a weight of the food product; a temperature sensor for detecting a temperature of the food product; a video capturing device configured to capture at least one image of the food product; one or more biosensors adapted to detect a chemical composition of the food product; or an air humidity sensor and a temperature sensor.

3. The production system according to claim 1, wherein the sensor comprises a video capturing device configured to capture at least one image of the food product and the processor is configured to recognize a type of the food product based on the at least one image captured.

4. The production system according to claim 1, wherein the processor is configured to compare the parameter regarding a property of the food product detected by the sensor with stored parameters.

5. The production system according to claim 1, wherein the processor is configured to combine the derived quality indication with the quality assessment entered by the user through the user interface, to calculate a final quality indication.

6. The production system according to claim 5, wherein the processor is configured to calculate, for the food product, a final quality indication based also on a mean final quality indication of a plurality of the food product controlled previously.

7. The production system according to claim 1, and further comprising a database, connected to the processor and configured to store at least one chosen from the derived quality indication or the detected value of the at least one parameter regarding the property of the food product.

8. The production system according to claim 1, wherein at least one output of the processor is defined by at least one of the control or adjustment signals.

9. The production system according to claim 1, wherein at least one input of the processor is the parameter representing the quality assessment of the food product, sent through the user interface of the feedback device.

10. A method comprising the following steps:
   detecting with a sensor at least one parameter regarding a property of a food product;
   deriving a quality indication of the food product based on a value detected by the sensor, the quality indication including information relating to a quality of the food product, expressed as an assessment of the quality, relating to the at least one parameter;
   transmitting the quality indication through a data communication network;
   providing a machine adapted to thermally treat the food product and including at least one actuator operating on the food product and a controller to control the at least one actuator;
   sending control signals to the controller and adjusting the at least one actuator as a function of the derived quality indication,
   combining the derived quality indication of the food product based on the detected value, the quality assessment of the food product obtained from a user during a self-learning mode, and an average final quality indication of preceding food products to obtain a final quality indication according to the following:

$$I_{fin}=(G_{op}+I_n)/I_{medn-1}$$

wherein,
$I_{fin}$ is the final quality indication of the food product;
$I_{medn-1}$ is the average final quality indication of the preceding food products;
$G_{op}$ is the quality assessment from the user in the self-learning mode; and
$I_n$ is the quality indication derived from the sensor.

11. The method according to claim 10, wherein the step of calculating the final quality indication of the food product comprises calculating, for the food product, a final quality indication based also on a mean of a previous plurality of the quality indication of the food product.

12. The method according to claim 10, wherein the step of detecting with the sensor the at least one parameter regarding the property of the food product comprises a step of capturing at least one image of the food product by a video capturing system, the method further comprising the step of: processing the at least one image captured by the video capturing system and, based on that at least one image, determining a type for the food product.

13. The method according to claim 10, wherein the step of detecting with the sensor the at least one parameter regarding the property of the food product comprises a step of detecting a temperature of the food product.

14. The method according to claim 10, wherein the step of detecting with the sensor the at least one parameter regarding the property of the food product comprises a step of detecting a weight of the food product.

15. The method according to claim 10, wherein the step of detecting with the sensor the least one parameter regarding the property of the food product comprises a step of detecting at least one chosen from a form, a shape, or a color of the food product.

16. The method according to claim 10, wherein the step of detecting with the sensor the at least one parameter regarding the property of the food product comprises a step of detecting a chemical composition of the food product.

17. The method according to claim 10, wherein the at least one actuator is a heating and/or cooling element and wherein the step of adjusting the at least one actuator as the function of the derived quality indication comprises a step of adjusting a thermal power of the heating and/or cooling element.

18. The method according to claim 10, wherein the step of adjusting the at least one actuator as the function of the derived quality indication comprises a step of adjusting a processing time of the food product in the machine.

19. The method according to claim 10, and further, comprising a step of measuring at least one parameter regarding base ingredients of the food product and/or a property of a processing environment.

20. The method according to claim 19, wherein the at least one parameter regarding the base ingredients and/or the property of the processing environment comprises at least one chosen from: weight, color, form, consistency, viscosity, transparency, volume, chemical composition, air humidity or temperature.

21. The method according to claim 19, wherein the at least one parameter regarding the base ingredients and the at least one parameter detected with the sensor relate to a same physical quantity, and wherein the method comprises a step of comparing measured values of the at least one parameter regarding base ingredients and the at least one parameter detected with the sensor.

22. The method according to claim 21, wherein the step of measuring the at least one parameter regarding the base ingredients comprises a step of measuring a weight of the base ingredients and wherein the step of detecting the at least one parameter regarding a property of the food product comprises a step of measuring a weight of the food product, the method further comprising a step of comparing the measured weight of the base ingredients with the measured weight of the food product.

* * * * *